US00PP34763P2

(12) United States Plant Patent
Hartman

(10) Patent No.: US PP34,763 P2
(45) Date of Patent: Nov. 22, 2022

(54) ***CALADIUM* PLANT NAMED 'CWH BRZ OF16-130'**

(50) Latin Name: ***Caladlium* X *hortulanum***
Varietal Denomination: 'CWH BRZ OF16-130'

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/741,070

(22) Filed: May 10, 2022

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — C. Anne Whealy

(57) ABSTRACT

A new and distinct cultivar of *Caladium* plant named 'CWH BRZ OF16-130', characterized by its intermediate to tall and upright to mounding plant habit; dense, leafy and bushy appearance; vigorous growth habit and rapid growth rate; fancy-type leaves that are dark olive green overlain with reddish bronze in color with pale orangish pink-colored blotches and dark green-colored blotches flushed with reddish bronze, and bright reddish pink-colored areas surrounding the venation; petioles that are reddish bronze in color; and tolerance to full sun conditions.

5 Drawing Sheets

Figure 1:
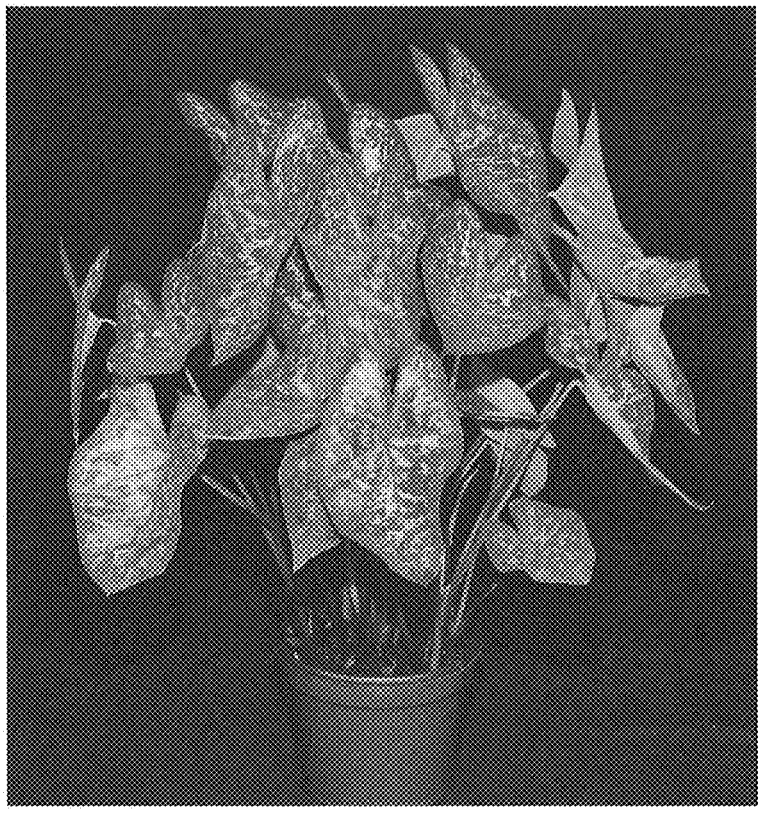

Botanical designation: *Caladium* X *hortulanum*.
Cultivar denomination: 'CWH BRZ OF16-130'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'CWH BRZ OF16-130'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2015 in Avon Park, Fla. of *Caladium* X *hortulanum* 'Southern Charm', disclosed in U.S. Plant Pat. No. 27,942, as the female, or seed, parent with *Caladium* X *hortulanum* 'Scarlet Flame', disclosed in U.S. Plant Pat. No. 25,419, as the male, or pollen, parent. The new *Caladium* plant was discovered and selected by the Inventor as a single plant within the progeny of the stated cross-pollination in a controlled outdoor nursery environment in Avon Park, Fla. in September, 2016.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2017 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'CWH BRZ OF16-130'.These characteristics in combination distinguish 'CWH BRZ OF16-130' as a new and distinct *Caladium* plant:

1. Intermediate to tall and upright to mounding plant habit; dense, leafy and bushy appearance.
2. Vigorous growth habit and rapid growth rate.
3. Fancy-type leaves that are dark olive green overlain with reddish bronze in color with pale orangish pink-colored blotches and dark green-colored blotches flushed with reddish bronze, and bright reddish pink-colored areas surrounding the venation.
4. Petioles that are reddish bronze in color.
5. Tolerant to full sun conditions.

Plants of the new *Caladium* differ primarily from plants of the female parent, 'Southern Charm', in the following characteristics:

1. Leaves of plants of the new *Caladium* are dark olive green overlain with reddish bronze in color with pale orangish pink-colored blotches and dark green-colored blotches flushed with reddish bronze, and bright reddish pink-colored areas surrounding the venation whereas leaves of plants of 'Southern Charm' are grey green in color with dark green-colored margins and red purple-colored venation and areas surrounding the venation.

2. Leaf petioles of plants of the new *Caladium* are reddish bronze in color whereas leaf petioles of plants of 'Southern Charm' are green in color and tinged with pink.

Plants of the new *Caladium* differ primarily from plants of the male parent, 'Scarlet Flame', in the following characteristics:

1. Plants of the new *Caladium* are taller than plants of 'Scarlet Flame'.
2. Plants of the new *Caladium* have fancy-type leaves whereas plants of 'Scarlet Flame' have lance-type leaves.
3. Leaves of plants of the new *Caladium* are dark olive green overlain with reddish bronze in color with pale orangish pink-colored blotches and dark green-colored blotches flushed with reddish bronze, and bright reddish pink-colored areas surrounding the venation whereas leaves of plants of 'Scarlet Flame' are dark green in color with rose red-colored venation and pink and rose red-colored spots and blotches.
4. Leaf petioles of plants of the new *Caladium* are reddish bronze in color whereas leaf petioles of plants of 'Scarlet Flame' are dark green in color densely covered with dark brown-colored streaks and stippling appearing almost black in color.

Plants of the new *Caladium* can be compared to plants of *Caladium* X *hortulanum* 'Carolyn Whorton', not patented. In side-by-side comparisons, plants of the new *Caladium* differ primarily from plants of 'Carolyn Whorton' in the following characteristics:

1. Leaves of plants of 'Carolyn Whorton' are flatter than and not as cupped as leaves of the new *Caladium*.
2. Leaves of plants of the new *Caladium* are dark olive green overlain with reddish bronze in color with pale orangish pink-colored blotches and dark green-colored blotches flushed with reddish bronze, and bright reddish pink-colored areas surrounding the venation whereas leaves of plants of 'Carolyn Whorton' are olive green in color with pink-colored blotches and bright red to rose pink-colored venation.
3. Leaf petioles of plants of the new *Caladium* are reddish bronze in color whereas leaf petioles of plants of 'Carolyn Whorton' are tannish pink and tannish green in color with darker-colored streaks, stippling and tessellations.

Plants of the new *Caladium* can also be compared to plants of *Caladium* X *hortulanum* 'Xplosion', disclosed in U.S. Plant Pat. No. 31,570. In side-by-side comparisons, plants of the new *Caladium* differ primarily from plants of 'Xplosion' in the following characteristics:

1. Plants of the new *Caladium* have fancy-type leaves whereas plants of 'Xplosion' have lance-type leaves.
2. Leaves of plants of 'Xplosion' are flatter than and not as cupped as leaves of the new *Caladium*.
3. Leaves of plants of the new *Caladium* are dark olive green overlain with reddish bronze in color with pale orangish pink-colored blotches and dark green-colored blotches flushed with reddish bronze, and bright reddish pink-colored areas surrounding the venation whereas leaves of plants of 'Xplosion' are dark green in color tinged with greyed purple with red purple to dark red-colored venation and interveinal areas that are white in color with light red-colored spots.
4. Leaf petioles of plants of the new *Caladium* are reddish bronze in color whereas leaf petioles of plants of 'Xplosion' are greyed red, green and greyed green in color with dark brown-colored streaks and stipples.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'CWH BRZ OF16-130' grown in a container that has had its tuber de-eyed prior to planting.

Figure 2:
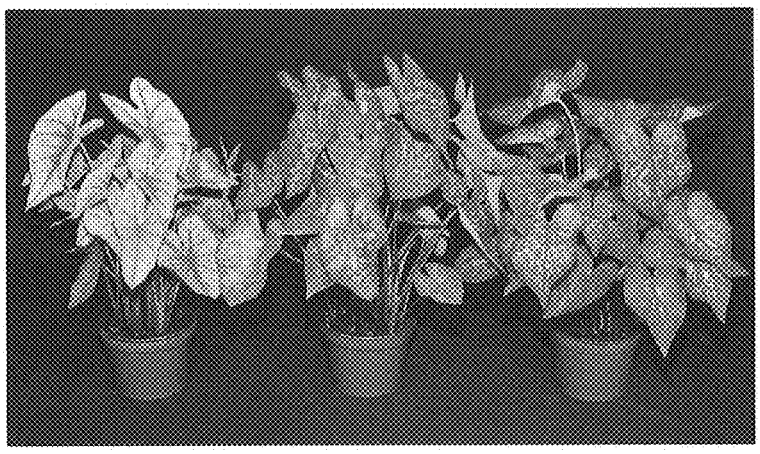

The photograph at the top of the second sheet (FIG. 2) is side perspective view of typical plants of the female parent, 'Southern Charm' (left), 'CWH BRZ OF16-130' (center) and the male parent, 'Scarlet Flame' (right).

Figure 3:
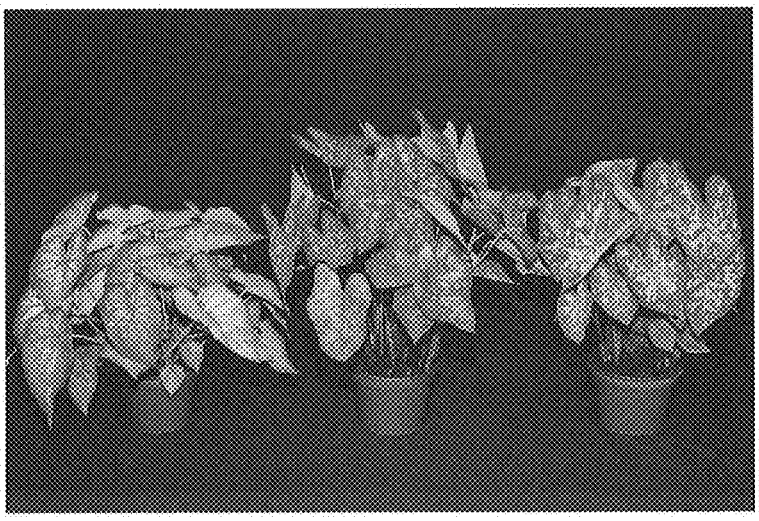

The photograph at the bottom of the second sheet (FIG. 3) is side perspective view of typical plants of 'Carolyn Whorton' (right), 'CWH BRZ OF16-130' (center) and 'Xplosion' (left).

Figure 4:
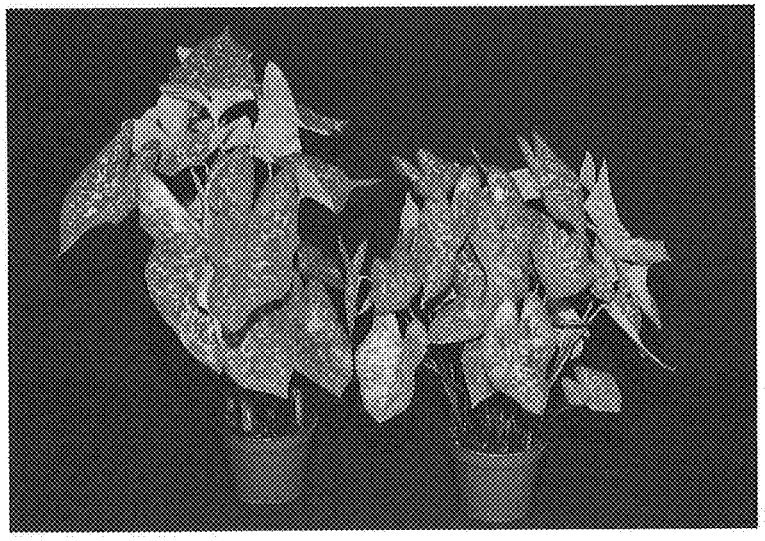

The photograph at the top of the third sheet (FIG. 4) is a comparison view of typical plants of 'CWH BRZ OF16-130' grown in containers, the plant on the left has not had its tuber de-eyed and the plant on the right has had its tuber de-eyed prior to planting.

Figure 5:
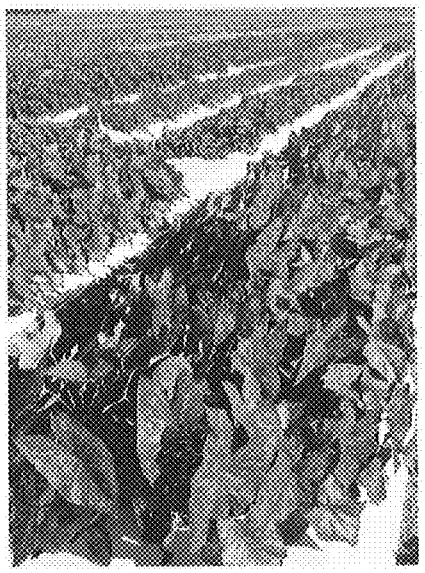

The photograph at the bottom of the third sheet (FIG. 5) is a side perspective view of typical plants of 'CWH BRZ OF16-130' grown in an open production field.

Figure 6:
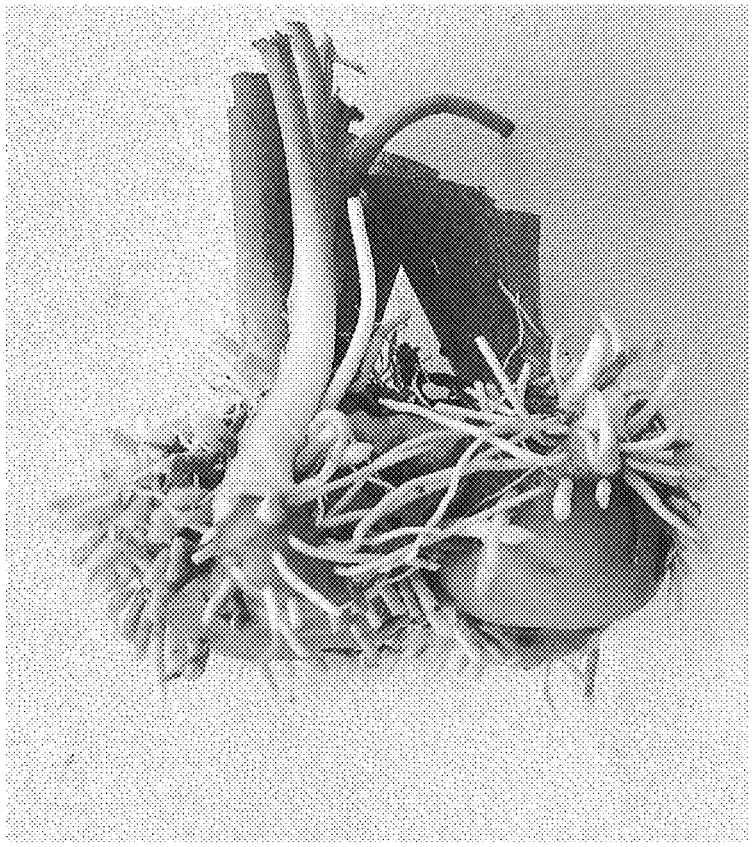

The photograph on the fourth sheet (FIG. 6) is a close-up view of typical freshly-harvested tubers with roots and leaf petioles of 'CWH BRZ OF16-130'.

Figure 7:
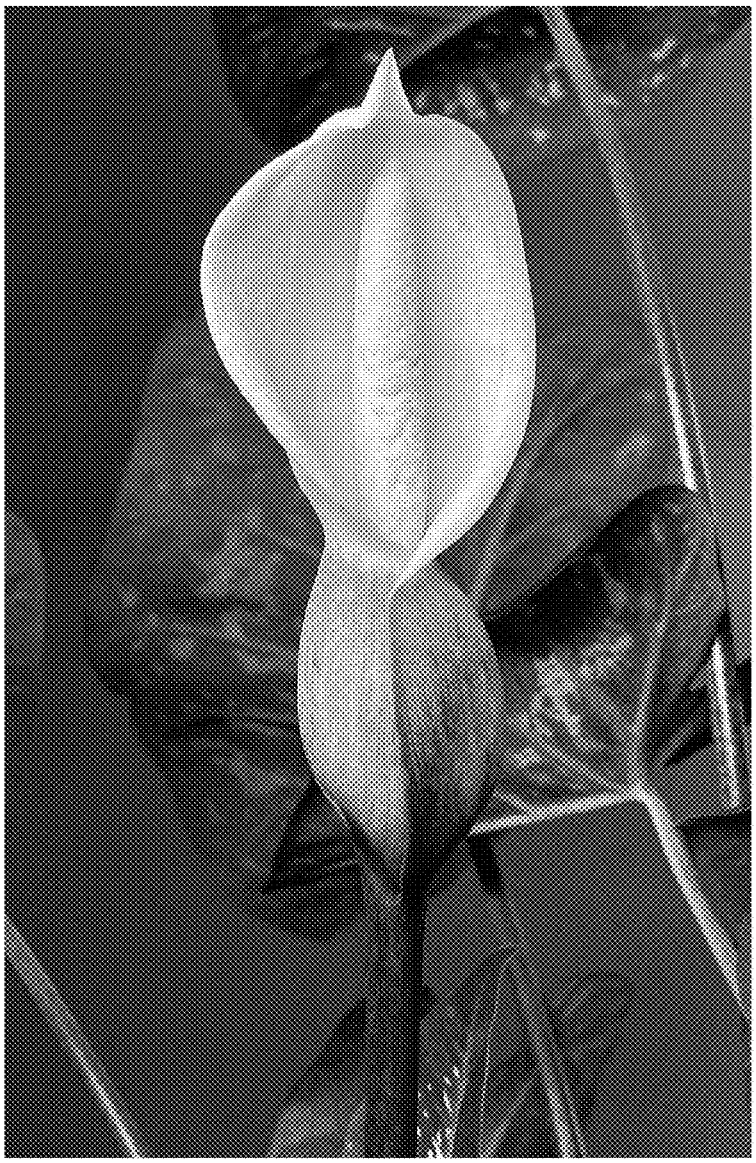

The photograph on the fifth sheet (FIG. 7) is a close-up view of a typical inflorescence of 'CWH BRZ OF 16-130'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were twelve weeks old and plants grown in the outdoor nursery were 4.5 to 6 months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'CWH BRZ OF16-130'.

PARENTAGE:

*Female, or seed, parent.*—*Caladium* X *hortulanum* 'Southern Charm' disclosed in U.S. Plant Pat. No. 27,942.

*Male, or pollen, parent.*—*Caladium* X *hortulanum* 'Scarlet Flame', disclosed in U.S. Plant Pat. No. 25,419.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments are round to ovate in shape. Height: About 3.2 cm to 3.6 cm. Diameter: About 5.4 cm to 8.3 cm. Segment height: About 2.9 cm to 3.2 cm. Segment diameter: About 4 cm to 5.2 cm. Axillary bud shape: Roughly triangular. Axillary bud height: About 5 mm. Axillary bud width: About 5.5 mm. Texture: Thick, starchy; somewhat brittle. Color: Periderm, freshly-harvested: Close to 199A and 199B. Periderm, dried: Close to 200A to 200B. Epidermis: Close to 158B and 158C; becoming closer to 161D with subsequent development. Cortical tissue: Close to 4D. Axillary buds: Close to 37D variably marked and tinged with close to 202A. Root description: Thick, fleshy contractile roots with few lateral branches; color, close to N155D, actual color of the roots is dependent on substrate composition, water quality, fertilizer type and formulation, substrate temperature and physiological age of roots. Rooting habit: Dense.

Plant description:

*Plant type*.—Herbaceous perennial; suitable as a potted plant in containers 15-cm to 25-cm and suitable as a landscape plant in shaded and full sunlight areas.

*Plant and growth habit*.—Intermediate to tall and upright to mounding plant habit; dense, leafy and bushy appearance; vigorous growth habit and rapid growth rate; potted plants finish in saleable form in about eight weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 46 cm to 49 cm.

*Plant height, from soil level to top of foliar plane, shade house-grown potted plants, tubers not de-eyed*.—About 50.8 cm to 53 cm.

*Plant height, from soil level to top of floral plane, shade house-grown potted plants, tubers not de-eyed*.—About 29 cm.

*Plant diameter or spread, shade house-grown potted plants, tubers de-eyed*.—About 43 cm to 48 cm.

*Plant diameter or spread, shade house-grown potted plants, tubers not de-eyed*.—About 43 cm to 45 cm.

*Number of shoots per plant, shade house-grown potted plants, tubers de-eyed*.—About four to five develop per #1 tuber.

*Number of shoots per plant, shade house-grown potted plants, tubers not de-eyed*.—About three to four develop per #1 tuber.

*Cataphylls, shade house-grown potted plants*.—Length: About 3.5 cm to 5.1 cm. Width: About 1 cm to 1.2 cm. Shape: Lanceolate or wedge-shaped. Apex: Variable, acute or emarginate. Base: Sheathing the stem. Texture and luster, outer and inner surfaces: Smooth, glabrous; semi-glossy. Color, outer surface: Close to 177D densely streaked and stippled with close to 200A and 200B; occasionally tinged with close to 147A; color becoming closer to 200B to 200C with subsequent development. Color, inner surface: Close to N155B and 49D, occasionally faintly flushed with close to 184B, with colors and color patterns from outer surface visible.

Leaf description:

*Arrangement and type*.—Alternate; simple; fancy-type.

*Length, shade house-grown potted plants, tubers not de-eyed*.—About 20 cm to 28 cm.

*Width, shade house-grown potted plants, tubers not de-eyed, flattened*.—About 12.2 cm to 16.5 cm.

*Shape*.—Ovate, cordate; leaves cupped proximally.

*Apex*.—Acuminate, acute.

*Base*.—Sagittate-peltate; cordate.

*Margin*.—Entire; mostly flat with broad undulations.

*Texture and luster, upper surface*.—Smooth, glabrous; leathery; dull to slightly glossy sheen.

*Texture and luster, lower surface*.—Smooth, glabrous; veins and areas surrounding the veins slightly glaucous; leathery; dull sheen.

*Venation pattern*.—Pinnate and palmate.

*Color, shade house-grown potted plants*.—When developing and fully expanded leaves, upper surface: Background color: Much darker than 147A variably flushed with close to N186C. Margins: Close to 187B. Basal notch: Close to 187A. Midvein and lateral venation: Close to 185A tinged with close to 53A; surrounding the veins, close to 183A and 181B. Blotches: When opening, close to 155C becoming closer to 39C, 182C and 185D with development. When developing and fully expanded leaves, lower surface: Background color: Close to 191A variably tinged with close to 189A. Margins: Close to 187C. Basal notch: Close to 187A. Midvein: Close to 182C densely streaked and blushed with close to 185A and 185B; surrounding the midvein, close to 182A and 184A. Lateral venation: Close to N187A and 181C; surrounding the veins, close to 182A and 184A. Spots and blotches: Close to 36A, 50D, 51C and N170D.

*Petioles*.—Aspect: Initially upright and straight and leaning outwardly with development; flexible. Length, shade house-grown potted plants: When tubers are de-eyed, about 24 cm to 38 cm. Length, shade house-grown potted plants: When tubers are not de-eyed, about 25 cm to 42 cm. Diameter, distally, shade house-grown potted plants: When tubers are de-eyed, about 2 mm to 4.5 mm. Diameter, proximally, shade house-grown potted plants: When tubers are de-eyed, about 5 mm to 9 mm. Texture and luster: Smooth, glabrous; glossy. Color, shade house-grown potted plants: Close to 181C and 181D flushed with close to 183B and 183C and variably tinged with close to 146A to 146B; with streaks and stippling, close to 200C variably and faintly tinged with close to 147A; just below the leaf junction, close to 182C with dense streaks and stippling, close to 185B. Wing length, shade house-grown potted plants: About 6.8 cm to 10 cm. Wing diameter, shade house-grown potted plants: About 7 mm to 9 mm. Texture and luster, inner surface: Smooth, glabrous; glossy. Texture and luster, outer surface: Smooth, glabrous; slightly glaucous, dull sheen. Wing color, shade house-grown potted plants: Inner surface: Close to N155C and 49D; distally, occasionally flushed and streaked with close to 184B; colors and patterns on the outer surface are visible on the inner surface. Outer surface: Close to 177D, densely streaked and stippled with close to 200A and 200B typically tinged with close to 147A.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about eight weeks after growth commences; inflorescences last about three days before fading; inflorescences persistent.

*Spathe*.—Length, overall: About 9.5 cm. Length, distal open portion: About 5.3 cm. Length, proximal closed portion: About 4.2 cm. Width, distal open portion: About 3.9 cm. Depth, distal open portion: About 1.5 cm. Width, at constriction: About 1.2 cm to 1.4 cm. Width, proximal closed portion: About 2.5 cm. Shape, open portion: Obovate. Apex: Cuspidate. Base: Acute. Margin: Entire; distally, reflexed. Texture and luster, front surface: Smooth, glabrous; distally, dull sheen, and proximally, glossy. Texture and luster, rear surface: Smooth, glabrous; dull sheen; proximally, slightly glaucous. Color, front surface: Distal open portion: Close to 155C; with variable and random areas faintly tinged with close to 187D; with subsequent development, distally becoming closer to 199A. Proximal closed portion: Close to 187A and 187B; color does not change with subsequent development. Color, rear surface: Distal open portion: Close to 155C, in the center, faintly flushed with close to 145D with sparse flecking, close to 187D; color does not change with subsequent development. Proximal closed portion: Close to 147C and 147D variably streaked with close to 138A; margins and constriction area are flushed with close to 183C and 183D; color does not change with subsequent development.

*Spadix*.—Length, overall: About 8 cm. Length, male flower zone: About 4.5 cm. Length, sterile zone: About 1.5 cm. Length, female flower zone: About 2 cm. Diameter, male flower zone: About 8 mm. Diameter, sterile flower zone: About 6 mm. Diameter, female flower zone: About 7 mm. Shape: Columnar, spindle-shaped. Apex: Rounded to acute. Base: Obtuse. Aspect: Upright. Color, mature, male zone: Close to 158D. Color, mature, sterile zone: Close to 158D. Color, mature, female zone: Close to 155D. Male flowers: Quantity per spadix: About 120. Shape: Obovate. Height: About 3 mm. Diameter: About 3 mm. Pollen amount: Abundant. Pollen color: Close to 4D. Female flowers: Quantity per spadix: About 95. Shape: Obovate. Height: About 3 mm. Diameter: About 2 mm. Stigma color: Close to 155D. Ovary color: Close to 158D.

*Scapes*.—Length: About 19.5 cm. Diameter: About 6.5 mm. Strength: Sturdy; somewhat flexible. Aspect: Mostly erect, straight. Texture and luster: Smooth, glabrous; glossy. Color: Close to 182B and 182C tinged with close to 177A with stippling, streaks and stripes, close to 200B and 200C; just below the spathe, close to 181D tinged with close to 48C and 48D and sparsely streaked with close to 146D tinged with 147D.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature & full sun tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring. Plants of the new *Caladium* have been observed to be tolerant to full sunlight conditions.

It is claimed:

1. A new and distinct *Caladium* plant named 'CWH BRZ OF16-130' as illustrated and described.

* * * * *